US00PP24700P3

(12) United States Plant Patent
Glen

(10) Patent No.: US PP24,700 P3
(45) Date of Patent: Jul. 29, 2014

(54) PEACH TREE NAMED 'ICE QUEEN'

(50) Latin Name: *Prunus persica*
Varietal Denomination: Ice Queen

(71) Applicant: Lowell Glen, Le Grand, CA (US)

(72) Inventor: Lowell Glen, Le Grand, CA (US)

( * ) Notice: Subject to any disclaimer, the term of this patent is extended or adjusted under 35 U.S.C. 154(b) by 29 days.

(21) Appl. No.: 13/694,611

(22) Filed: Dec. 13, 2012

(65) Prior Publication Data

US 2014/0173793 P1 Jun. 19, 2014

(51) Int. Cl.
*A01H 5/00* (2006.01)

(52) U.S. Cl.
USPC ..... Plt./196

(58) Field of Classification Search
CPC .. A01H 5/0868; A01H 5/0856; A01H 5/0837
USPC ..... Plt./196
See application file for complete search history.

(56) References Cited

U.S. PATENT DOCUMENTS

PP12,570 P2 4/2002 Bradford

*Primary Examiner* — Kent L Bell

(57) ABSTRACT

The present invention relates to a new and distinct variety of peach tree, *Prunus persica*, broadly characterized by a large size, vigorous, hardy, self-fertile, productive and regular bearing tree. The variety blooms during the early to mid season and requires about 450 chilling hours. The fruit matures under the ecological conditions described in the last half of July, with first picking on Jul. 20, 2012. The fruit is uniform, large in size, globose in shape, freestone in type, firm and melting in texture, white in flesh color, almost full red in skin color, and a tasty balance of light acid and sugar in flavor.

1 Drawing Sheet

Botanical classification: *Prunus persica.*
Variety denomination: 'ICE QUEEN'.

BACKGROUND OF THE VARIETY

In a continuing effort to improve the quality of shipping fruits, I, the inventor, typically hybridize a large number of peach, nectarine, plum, apricot, and cherry seedlings each year. I also grow a smaller number of open pollinated seeds of each of these fruits, usually to capture recessive traits. The present invention relates to a new and distinct variety of peach tree, which has been denominated varietally as 'Ice Queen'.

The present variety was hybridized by me in 2000 as a first generation cross using 'Snow Princess' (U.S. Plant Pat. No. 12,570) peach as the selected seed parent and an unnamed yellow flesh nectarine (unpatented) as the selected pollen parent. The fruit of this cross was gathered that summer, and the seeds were removed, cracked, stratified, germinated, and grown as seedlings on their own root in my greenhouse. Upon reaching dormancy the seedlings were transplanted as a group to a cultivated area of my experimental orchard located near Le Grand, Calif., in Merced County (San Joaquin Valley). During the fruit evaluation season of 2004 I selected the present variety as a single tree from the group of seedlings described above. Subsequent to origination of the present variety of peach tree, I asexually reproduced it by budding and grafting in the experimental orchard described above, and such reproduction of tree and fruit characteristics were true to the original tree in all respects. The reproduction of the variety included the use of 'Nemaguard' (unpatented) rootstock upon which the present variety was compatible and true to type.

The present variety is similar to its unnamed pollen parent in several aspects, such as being a productive tree with large pink blossoms and reniform glands, but it is quite distinguished therefrom by producing white flesh freestone peaches instead of yellow flesh clingstone nectarines.

The present variety is most similar to its seed parent 'Snow Princess' peach (U.S. Plant Pat. No. 12,570) by having a vigorous tree with large blossoms and reniform leaf glands, being self-fertile, and producing white flesh freestone peaches that are large in size, mostly red in skin color, globose in shape, and firm in texture, but is distinguished therefrom by producing fruit that matures about seven days earlier, that is somewhat sweeter in flavor, and that has a flavor that is a balance between light acid and sugar, rather than sub-acidic. It is to be noted that the claimed ripening time for 'Snow Princess' peach in U.S. Plant Pat. No. 12,570 was Jul. 20, 2000. It has been determined during subsequent years that the ripening time for 'Snow Princess' peach is usually near August 1st, with the actually date of first pick recorded this year as Jul. 27, 2012.

SUMMARY OF VARIETY

In summary, the present variety is characterized by a large size, vigorous, hardy, self-fertile, productive and regular bearing tree. The variety blooms during the early to mid season and requires about 450 chilling hours. The fruit matures under the ecological conditions described in the last half of July, with first picking on Jul. 20, 2012. The fruit is uniform, large in size, globose in shape, freestone in type, firm and melting in texture, white in flesh color, almost full red in skin color, and a tasty balance of light acid and sugar in flavor.

DRAWING

The accompanying photograph consists of four whole fruits positioned to display the characteristics of the skin color and form, one divided fruit to reveal the flesh and stone, three insets to reveal buds and blossoms, and typical leaves.

POMOLOGICAL CHARACTERISTICS

Referring now more specifically to the pomological characteristics of this new and distinct variety of peach tree, the following has been observed under the ecological conditions prevailing near Le Grand, Merced County (San Joaquin Valley), Calif., and was developed at the state of firm ripe on Jul. 28, 2012, on the original tree during its twelfth growing season. The blossom and flower descriptions were made the previous blooming season. All major color code designations are by reference to the Inter-Society Color Council, National Bureau of Standards. Common color names are also used occasionally.

PARENTAGE

Seed parent: 'Snow Princess' (U.S. Plant Pat. No. 12,570) peach.

Pollen parent: Unnamed nectarine (unpatented).

TREE

Size: Large, reaching and maintaining a height of 8' [2.44 m.] and a spread of 8' [2.44 m.] after twelve growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Spreading and dense.

Form: Vase type.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning necessary.

Fertility: Self-fertile.

Bearing: Regular bearer with no alternate bearing yet observed.

Approximate chilling requirement: 450 hours.

Trunk:

- *Size.*—Stocky, reaching a maximum diameter of 6" [152.4 mm.] after the twelfth growing season.
- *Texture.*—Shaggy.
- *Bark color.*—A Moderate yellowish brown [77. m.yBr] and Grayish brown [61. gy.Br] variegation with Brownish gray [64. brGy] crevices present.
- *Lenticels.*—Approximate Number Per Square Inch: 10. Color: Brownish orange [54. brO]. Size: ¼" [6.4 mm.] to 7/16" [11.1 mm.] in length. Diameter is typically one fourth as much as the length. Shape: Eye-shaped, elongated.

Branches:

- *Size.*—Diameter of main scaffold is 3" [76.2 mm.] measured 12" above the crotch, diameter of limb is 1½" [38.1 mm.] measured 12" above the first fork.
- *Texture.*—Smooth on first and second year wood, increasing roughness with age.
- *Color.*—1st Year Wood Topside: Grayish red [19. gy.R]. 1st Year Wood Underside: Brilliant yellow green [116. brill.YG]. Older Wood: A Grayish brown [61. gy.Br] and Light grayish brown [60. l.gy.Br] variegation.
- *Lenticels.*—Number Per Square Inch: More than 50 on second year wood. Color: Strong brown [55. s.Br]. Size: 1/64" [0.4 mm.] to 1/16" [1.6 mm.] in length on second year wood. Diameter is typically one fourth as much as the length. Shape: Rectangular, elongated.

Leaves:

- *Size.*—Medium. Average Length: 6" [152.4 mm.]. Average Width: 1⅜" [34.9 mm.].
- *Arrangement.*—Alternate.
- *Thickness.*—Medium.
- *Form.*—Elliptical.
- *Apex.*—Acuminate.
- *Base.*—Rounded to slightly acute.
- *Surface.*—Smooth.
- *Color.*—Dorsal Surface: Moderate olive green [125. m.OlG]. Ventral Surface: Moderate yellow green [120. m.YG].
- *Margin.*—Finely serrate.
- *Venation.*—Pinnately net veined.
- *Vein color.*—Light yellow green [119. l.YG].
- *Petiole.*—Average Length: ½" [12.7 mm.]. Average Thickness: 1/16" [1.6 mm.]. Color: Brilliant yellow green [116. brill.YG].
- *Stipules.*—Number: Usually 2 per leaf, up to 6 per growing tip. Average Length: ¼" [6.4 mm.]. Color: Moderate yellow green [120. m.YG] becoming Dark yellowish brown [78. d.yBr] with maturity.
- *Glands.*—Number: 2 to 6 per leaf. Position: Alternately positioned on petiole and base of blade. Size: Medium. Form: Reniform. Color: Brilliant yellow green [116. brill.YG] acquiring a Dark brown [59. d.Br] center with age.
- *Leaf buds.*—Pointed, medium in size.

Flower buds:

- *Hardiness.*—Hardy, with respect to central California winters.
- *Diameter.*—Typically ⅜" [9.5 mm.] 1 week before bloom.
- *Length.*—Typically ⅝" [15.9 mm.] 1 week before bloom.
- *Form.*—Not appressed.
- *Surface.*—Pubescent.
- *Tip color.*—Moderate purplish pink [250. m.pPk].

Flowers: Perfect, complete, perigynous, usually a single pistil, typically thirty or more stamens, five sepal and petal locations alternately positioned.

- *Type.*—Showy, large.
- *Average flower diameter.*—2⅛" [54.0 mm.].
- *Average flower depth.*—½" [12.7 mm.] when fully open.
- *Number of petals.*—Mostly five, with a few petal fragments or double blossoms.
- *Petal shape.*—Circular to oval.
- *Petal margin.*—Entire, slightly wavy with a few notches.
- *Average petal diameter.*—13/16" [20.6 mm.].
- *Average petal length.*—⅞" [22.2 mm.].
- *Petal apex.*—Rounded.
- *Petal base.*—Rounded to somewhat truncate.
- *Petal color.*—Pale pink [7. p.Pk] toward the apex, Light purplish pink [249. l.pPk] toward the base on both sides.

*Anther color.*—Deep reddish orange [36. deep rO] over a Light yellow [86. l.Y] center at bloom onset.
*Stigma color.*—Pale yellow green [121. p.YG].
*Sepal color.*—Dark purplish red [259. d.pR] on the outer surface. The inner surface is a somewhat translucent Pinkish white [9. pk White] with both Grayish purplish red [262. gy.pR] and Vivid yellow green [115. v.YG] areas visible.
*Sepal outer surface.*—Pubescent.
*Sepal length.*—¼" [6.4 mm.].
*Sepal width.*—3/16" [4.8 mm.].
*Sepal apex.*—Rounded to elliptical to match the sepal length and width.
*Sepal margin.*—Fairly smooth.
*Average pistil length.*—1 1/16" [17.5 mm.].
*Average stamen length.*—9/16" [14.3 mm.].
*Fragrance.*—Moderate.
*Blooming period.*—Medium, the same as 'Snow Princess' (U.S. Plant Pat. No. 12,570) peach.
*Onset of bloom.*—One percent on Feb. 18, 2012.
*Date of full bloom.*—Mar. 1, 2012.
*Duration of bloom.*—One to two weeks, dependent on ambient temperature.
*Number per cluster.*—1 to 3 with single flowers most common.

FRUIT

Maturity when described: Firm ripe, Jul. 28, 2012.
Date of first picking: Jul. 20, 2012.
Date of last picking: Jul. 30, 2012.
Size: Uniform, large.
*Average diameter axially.*—2⅞" [73.0 mm.].
*Average diameter across suture plane.*—3⅛" [79.4 mm.].
*Average diameter across cheek plane.*—3⅛" [79.4 mm.].
*Typical weight.*—10.3 ounces [292 grams].
Form: Uniform, globose, symmetrical.
*Longitudinal section form.*—Slightly oblate.
*Axial view.*—Round.
Suture: An inconspicuous line located in a shallow groove that extends from the base, along the side, to just beyond the pistil point.
*Near the base.*—A sharp groove.
*Along the side.*—A shallow trough.
*Near the apex.*—A shallow groove.
Ventral surface: Rounded, slightly lipped toward the apex on both sides.
Lips: Slightly unequal.
Cavity: Flaring, elongated in the suture plane, suture showing on one side, Yellowish white [92. yWhite] stem markings typical.
*Depth.*—¾" [19.1 mm.].
*Breadth.*—1 5/16" [33.4 mm.].
Base: Truncate.
Apex: Rounded.
Pistil point: Negligible in length, usually depressed within the suture.
Stem: Medium.
*Average length.*—7/16" [11.1 mm.].
*Average width.*—3/16" [4.8 mm.].
Skin:
*Thickness.*—Medium.
*Surface.*—Pubescent.
*Tenacity.*—Tenacious to flesh.
*Astringency.*—Non-astringent.
*Tendency to crack.*—None observed in dry season.
*Color.*—Very dark red [17. v.d.R] over a Moderate pink [5. m.Pk] background with some areas of Yellowish white [92. yWhite] where protected from the sun.
*Down.*—Moderate, very short, does not roll up when rubbed.
Flesh:
*Color.*—White [263. White] with a Yellowish white [92. yWhite] background acquiring some Moderate red [15. m.R] streaking toward stone with maturity.
*Surface of pit cavity.*—Covered with Dark red [16. d.R] to Moderate pink [5. m.Pk] fibers.
*Amygdalin.*—Scarce.
*Juice.*—Moderate, rich.
*Texture.*—Very firm, crisp, melting.
*Fibers.*—Abundant, fine, tender.
*Ripens.*—Somewhat earlier toward the apex.
*Flavor.*—A tasty balance of light acid and sugar, typically 16 to 20 brix.
*Aroma.*—Slight.
*Eating quality.*—Very good.

STONE

Type: Freestone.
Form: Oval.
Hilum: Narrow.
Base: Slightly oblique.
Apex: Acuminate.
Sides: Fairly equal.
Surface: Irregularly furrowed toward the apex, pitted toward the base.
Ridges: Jagged.
External color: Dark reddish brown [44. d.rBr].
Pit wall color when cracked: Moderate reddish brown [43. m.rBr].
Cavity surface color: Strong yellowish brown [74. s.yBr].
Average pit wall thickness: ¼" [6.4 mm.].
Average width: 1⅛" [28.6 mm.].
Average length: 1½" [38.1 mm.].
Average breadth: 13/16" [20.6 mm.].
Tendency to split: Very slight.
Kernel:
*Form.*—Oval.
*Skin color.*—Pale greenish yellow [104. p.gY] when first removed.
*Pellicle color.*—Dark grayish brown [62. d.gy.Br].
*Vein color.*—Light yellowish brown [76. l.yBr].
*Taste.*—Bitter.
*Viable.*—Yes.
*Average width.*—½" [12.7 mm.].
*Average length.*—¾" [19.1 mm.].
*Amygdalin.*—Moderate.

USE

Market: Fresh market and long distance shipping.
Keeping quality: Good, fruit quality observed to remain in good condition after 17 days in standard cold room at 36° Fahrenheit [2° Celsius].

Shipping quality: Good.
Resistance to insects: No unusual susceptibilities noted.
Resistance to diseases: No unusual susceptibilities noted.

OTHER NOTES

Although the new variety of peach tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of peach tree, substantially as illustrated and described, that is most similar to its seed parent 'Snow Princess' peach (U.S. Plant Pat. No. 12,570) by having a vigorous tree with large blossoms and reniform leaf glands, being self-fertile, and producing white flesh freestone peaches that are large in size, mostly red in skin color, globose in shape, and firm in texture, but is distinguished therefrom by producing fruit that matures about seven days earlier, that is somewhat sweeter in flavor, and that has a flavor that is a balance between light acid and sugar, rather than sub-acidic.

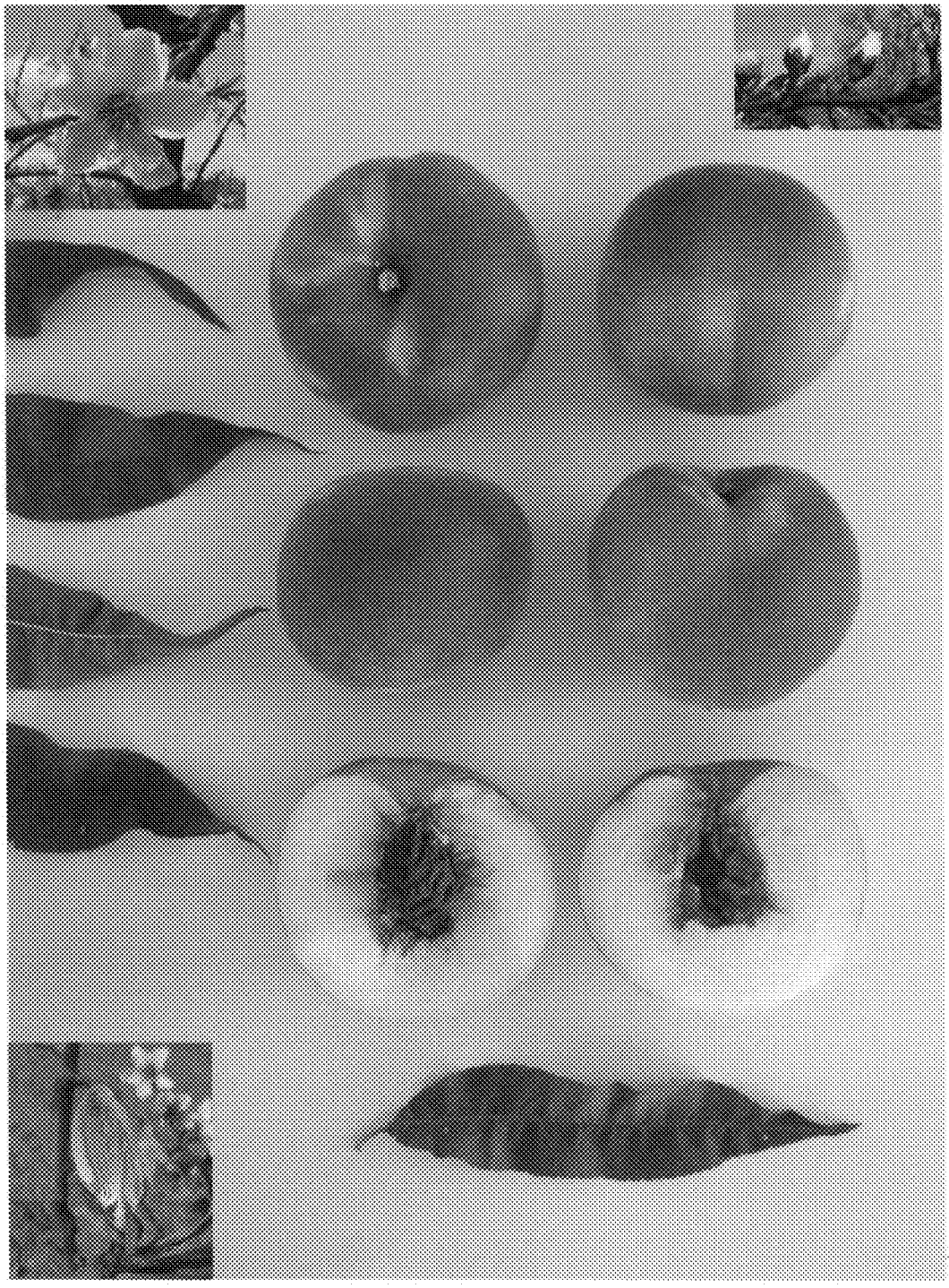

* * * * *